Figure 1A:
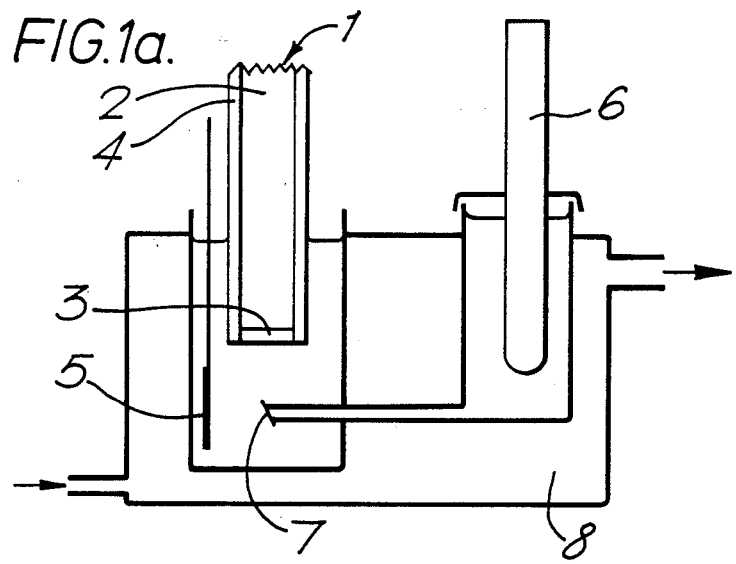

United States Patent [19]

Forrest et al.

[11] Patent Number: 4,945,045
[45] Date of Patent: Jul. 31, 1990

[54] ELECTROCHEMICAL METHODS OF ASSAY

[75] Inventors: Gordon C. Forrest, East Morsley; Simon J. Rattle, Quainton; Grenville A. Robinson, London; Hugh A. O. Hill, Oxford, all of England

[73] Assignee: Serono Diagnostics Ltd., England

[21] Appl. No.: 212,043

[22] Filed: Jun. 23, 1988

Related U.S. Application Data

[63] Continuation of Ser. No. 733,514, May 13, 1985, abandoned.

[30] Foreign Application Priority Data

Jul. 6, 1984 [GB] United Kingdom ............... 8417301

[51] Int. Cl.$^5$ .................... C12Q 1/26; G01N 27/26
[52] U.S. Cl. ..................... 435/25; 204/403; 435/7; 435/14; 435/26; 435/817; 436/806
[58] Field of Search .............. 435/7, 14, 25, 817; 436/806, 808; 204/403

[56] References Cited

U.S. PATENT DOCUMENTS

| | | |
|---|---|---|
| 3,966,556 | 6/1976 | Rubenstein et al. |
| 4,081,334 | 3/1978 | Suzuki ................... 204/403 |
| 4,233,144 | 11/1980 | Pace et al. |
| 4,319,980 | 3/1982 | Boguslaski et al. |
| 4,340,448 | 7/1982 | Schiller ................ 435/817 |
| 4,391,904 | 7/1983 | Litman .................. 435/7 |
| 4,545,382 | 10/1985 | Higgins ................ 204/403 |
| 4,600,690 | 7/1986 | Karmen ................. 435/7 |
| 4,758,323 | 7/1988 | Davis et al. ........... 435/817 |

FOREIGN PATENT DOCUMENTS

| | | |
|---|---|---|
| 0078636 | 5/1983 | European Pat. Off. |
| 0125136 | 11/1984 | European Pat. Off. |
| 0125139 | 11/1984 | European Pat. Off. |
| 0125867 | 11/1984 | European Pat. Off. |
| 0142301 | 5/1985 | European Pat. Off. |
| 0149339 | 7/1985 | European Pat. Off. |
| 8417301 | 7/1984 | United Kingdom . |

OTHER PUBLICATIONS

"Electron-Transfer Reactions Associated with Host--Guest Complexation. Oxidation of Ferrocenecarboxylic . . . " by T. Matsue, et al., J. Am. Chem. Soc, 1985, 107, pp. 3411–3417.
"Evaluation of Mediator–Titrants for the Indirect Coulometric . . . " by Robert Szentrimay et al., Electrochemical Studies of Biological Systems, pp. 143–169.
Itagaki Chem. Pharm. Bull 31(4), pp. 1283–1288 (1983).
Alexander, Anal. Chem. 1982, 54, pp. 68–71.
Eggers, Clin. Chem. 28(9) pp. 1848–1851 (1982).
Yolken Reviews of Infectious Diseases 4(1), pp. 35–42 (1982).

Primary Examiner—Sam Rosen
Attorney, Agent, or Firm—Ostrolenk, Faber, Gerb & Soffen

[57] ABSTRACT

A ligand in a sample can be assayed using electrochemical apparatus containing a working electrode and components comprising:

(a) the sample,
(b) a specific binding partner to the ligand, or a specific binding partner to the ligand and selected from ligand analogues and specific binding partners, and
(c) an electron-source or electron-acceptor; at least one of components (b) being labelled with an electron-transfer mediator capable of aiding the transfer of electrons between the electron-source or electron-acceptor and the working electrode by accepting electrons from the electron-source and donating them to the working electrode, or accepting the electrons from the electrode and donating them to the electron-acceptor.

The method includes the step of determining whether, and, if desired, the extent to which, the said transfer of electrons is perturbed by at least one of (i) formation of a complex of said ligand with a specific binding partner and (ii) controlled external influence which produces a perturbation of said transfer of electrons as a function of said complex formation.

23 Claims, 3 Drawing Sheets

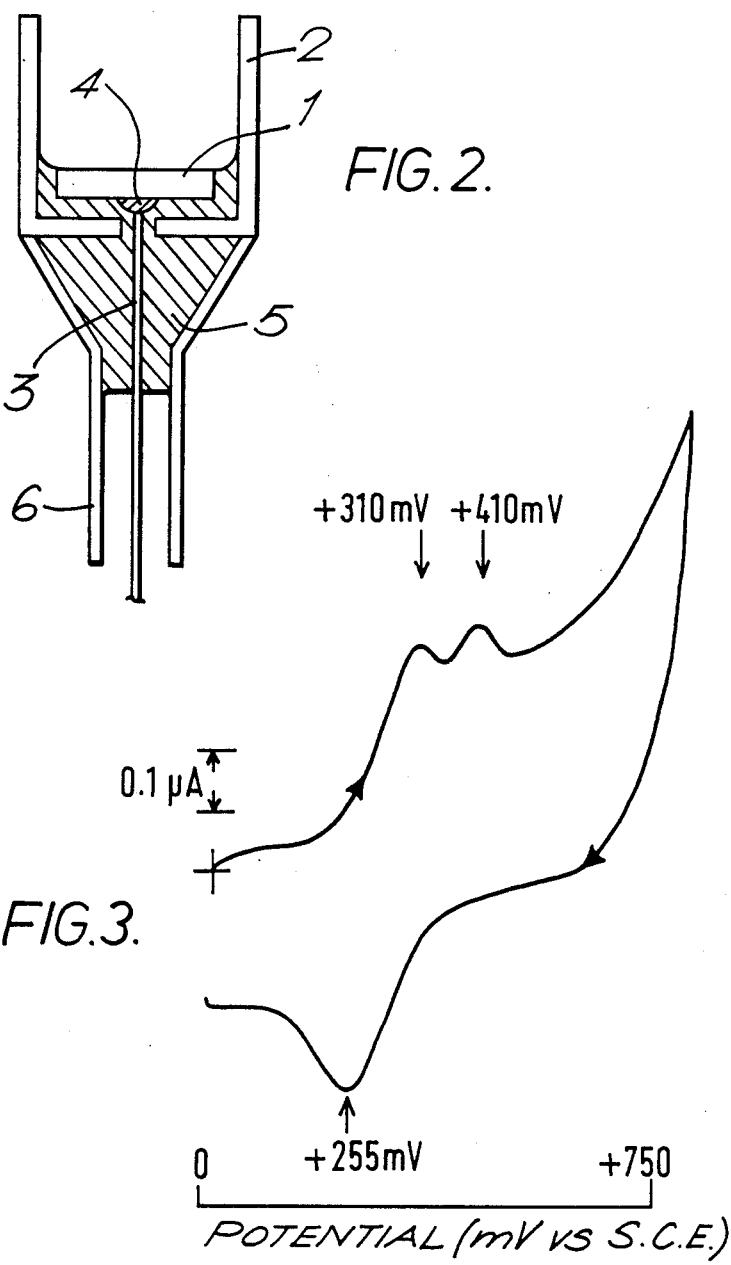

ELECTROCHEMICAL METHODS OF ASSAY

This is a continuation of application Ser. No. 733,514 filed on May 13, 1985, now abandoned.

The present invention relates to methods of assay of one of a pair of specific binding partners, and to kits of reagents for carrying out these methods.

There is today a great need for rapid and accurate methods of assaying biologically active substances (which may be at low concentration), particularly in body fluids such as blood, saliva or urine. A wide variety of medical conditions, such as pregnancy, drug overdose, metabolic birth defects, hormonal disorders and diabetes can be diagnosed using such assay techniques.

Many assay methods rely on the formation of a complex between the species under assay (hereinafter called "ligand") and another species to which it will bind specifically (hereinafter called "specific binding partner"). The extent of complex formation is a function of the amount of the ligand present.

The assay of ligand is determined by monitoring the extent of complex formation, for example by the use of chemical or biochemical labels. Several methods of labelling have been employed, for example radioisotopic or enzyme labelling, spin-labelling or labelling employing fluorescent or bioluminescent species.

The use of radioisotopic labels has been particularly widespread, due to the high degree of sensitivity and specificity obtainable. There are, however, serious disadvantages to the use of radioactive labels. Radioactive labels have limited shelf life due to spontaneous decay, necessitating frequent recalibration of the equipment, and their use requires adherence to strict safety precautions and is subject to legal regulation. These disadvantages inevitably lead to higher costs and necessity for high standards of sophistication of equipment, laboratory facilities and personnel.

We have now found that electron-transfer mediators which are capable of aiding the transfer of electrons from an electron-source to an electrode (or the transfer of electrons from the electrode to an electron-acceptor) may be employed as labels to overcome the problems associated with known labels as discussed above and to provide a sensitive, specific and convenient assay method.

Thus, in its broadest aspect, the present invention provides a method of assaying a ligand in a sample using electrochemical apparatus containing an electrode and components comprising:
(a) the sample,
(b) a specific binding partner to the ligand,
(c) if desired, at least one further reagent selected from ligand analogues (as herein defined) and specific binding partners, and
(d) an electron-source or electron-acceptor; at least one of components (b) and, if present, (c) being labelled with an electron-transfer mediator capable of aiding the transfer of electrons from the electron-source to the electrode, or from the electrode to the electron-acceptor, which method includes the step of determining whether, and, if desired, the extent to which, the said transfer of electrons is perturbed by complex formation and/or by controlled external influences.

The method of the present invention can be used for either qualitative or quantitative assays, the assay being completed by comparing the determined perturbation with calibration data.

The term "ligand analogue" used herein refers to a species capable of complexing with the same specific binding partner as the ligand under assay, and includes inter alia within its scope a known quantity of the ligand under assay.

Electron-sources or acceptors comprising component (d) may be single species or two or more co-operating species. Thus, for example, ascorbate

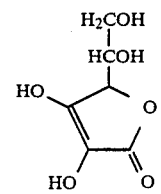

may function as an electron-source, apomorphine, substituted catechols (such as 1-amino-2-(3,4-dihydroxyphenyl)-ethane or 1-amino-2-(3,4,5-trihydroxyphenyl)-ethane) or aminophenols (such as p-aminophenol or 1-amino-2-(2-amino-4,5-dihydroxyphenyl)-ethane) suitably being employed as labels for components (b) and, if present, (c), or dihydronicotinamide adenosine diphosphate (NADH) may function as an electron-source, with quinones (eg o-quinones such as the oxidised forms of dopamine (3-hydroxytyramine) and 3, 4-dihydroxybenzylamine) as labels.

Alternatively, enzymes in co-operation with their substrates may be employed. Particularly suitable enzymes include the so-called oxido-reductases, particularly, but not exclusively, flavo- and quino- protein enzymes, e.g. glucose oxidase, glucose dehydrogenase or methanol dehydrogenase. The term "enzyme" used herein includes true enzymes, e.g. of the types previously mentioned, and apoenzymes which may become activated in the presence of a cofactor. As an apoenzyme, for example, apoglucose oxidase may be used.

Other electron-sources and acceptors and suitable mediators therefor are known in the art.

The preferred electron-sources are oxidoreductase enzymes (e.g. those mentioned above). Thus according to a preferred feature, the present invention provides a method of assaying a ligand in a sample as hereinbefore defined, wherein component (d) is an oxidoreductase enzyme in co-operation with a substrate therefor.

Suitable labels for components (b) and (c) for use in such a preferred method may, for example, be capable of accepting electrons from the enzyme and donating them to the electrode (during substrate oxidation), or may be capable of accepting electrons from the electrode and donating them to the enzyme (during substrate reduction). Such labels may, for example be selected from the following:

(i) a polyviologen such as, for example, a compound of formula

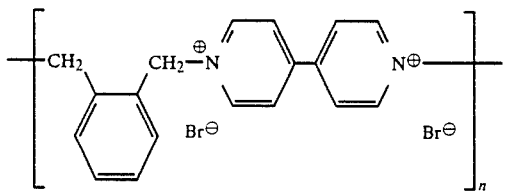

and derivatives thereof, e.g. side-chain alkyl derivatives, the preparation of which is described in Polymer Letters 9 pp 289-295 (1971), (ii) a low molecular weight compound selected from chloranils, fluoranils and bromanils (e.g. o-chloranil), (iii) ferrocene (bis-n$^5$-cyclopentadienyl iron (II)) or a derivative thereof [including e.g. functionalised derivatives such as ferrocene monocarboxylic acid (FMCA), polymeric forms ('polyferrocenes') such as (ferrocene)$_4$ or polyvinyl ferrocene and 'boron tetraferrocene' (B(ferrocene)$_4$)], (iv) compounds of biological origin possessing suitable enzyme compatability, e.g. Vitamin K, (v) N,N,N',N'-tetramethyl-4-phenylenediamine, and (vi) derivatives of phenazine methosulphate or phenazine ethosulphate, and of the apoenzyme;

Mediators may interact with the enzyme at a site remote from or near to the active site for the substrate reaction.

Of the aforementioned electron-transfer mediators, the preferred are ferrocene and functionalised derivatives thereof. These compounds are desirable for this purpose because they are relatively cheap, stable, water soluble, non-toxic, and provide an easily electrochemically reversible system which in its reduced Fe$^{II}$ state is not susceptible to oxidation by oxygen in the atmosphere.

Functionalisation may be required e.g. to permit attachment of the label to the reagent molecule. The redox potential of ferrocene is +422 mV vs NHE. By introducing functional groups on to the ring system, this figure can be varied between +300 and +650 mV. Moreover, the water-solubility of carboxy-substituted ferrocenes is greater than that of the parent compound (see, e.g. Szentrimay, R., 1977, Amer. Chem. Soc. Symposium Series, 38, 154).

Thus, for example, in the case of ferrocene, it may be necessary to modify the ferrocene complex by providing one or both of the cyclopentadienyl groups with one or more side chains, e.g. of the formula

—CHO

—(CH$_2$)$_n$COOH or

—(CH$_2$)$_m$NHR$^1$R$^2$ where n and m may be e.g. from 0 to 6 and R$^1$ and R$^2$, which may be the same or different, each represents hydrogen or an alkyl group containing 1 to 4 carbon atoms (e.g. methyl). Additional functional groups may be incorporated into the side chain, typically those groups used in the chemical modification of proteins, for example mercuric chloride, precursors of nitrenes and carbenes, diazo or iodide groups. Similar functionalisation may be desirable when mediators other than ferrocene are used.

The interaction between the mediator label and the enzyme may thus take the form of chemical bonding, or may take the form of non-chemical bonding or non-bonding interaction.

The working electrode from which the electrochemical readings will be taken will preferably be solid and have an electrically conductive working surface of e.g. carbon (preferably graphite, e.g. pyrolytic graphite), or metal, e.g. silver, gold or platinum. If the electrode is of carbon, it may be present as a pre-formed rod or as an electrode shape made up of a paste of carbon particles. The nature of the surface of the electrode is usually important. If metal, the surface can be roughened or chemically modified; if solid carbon, the surface can be previously heat-treated in a oven with oxygen excess or oxidized electrochemically. Thus, for example, when ascorbate is used as an electron-source, a carbon paste electrode of polished 'glassy carbon' sheets may advantageously be employed.

In addition to the working electrode from which the electrochemical readings will be taken, the apparatus may comprise an auxiliary (counter) electrode and optionally a reference electrode, the electrodes being used in conjunction with a potentiostat and a sensitive current meter. The apparatus preferably contains an aqueous assay medium comprising inter alia pH buffer. Means may be provided for incubating the assay medium at any desired temperature. A suitable electrochemical apparatus is illustrated in vertical cross-section in FIG. 1(a) of the accompanying drawings. The working electrode 1 is composed of an elongate core 2 of steel tipped with a working surface 3 of pyrolytic graphite and having a coating 4 of epoxy resin. The auxiliary (counter) electrode 5 is of platinum. A calomel reference electrode 6 is shown, connected to the cell via a luggin capillary 7. The cell and reference electrode are enclosed in a water jacket 8.

A variety of electrochemical methods exploiting any two of the three parameters potential (E), current (i) and time (t) may be used to measure the electrochemical characteristics of the components. For example, electrochemical measurements can be made using differental pulse voltammetry, cyclic voltammetry or squareware voltammetry. When cyclic voltammetry is used, a circuit such as, for example, that shown schematically in FIG. 1(b) of the accompanying drawings may be employed. In this Figure, C represents the auxiliary (counter) electrode, W the working electrode and R the reference electrode. This circuit may conveniently be used in conjunction with apparatus of the type shown in FIG. 1(a), the electrochemical current i being measured using a potentiostat.

In homogeneous assay systems, the formation of the complex between the ligand and the specific binding partner or, in the case of competitive assays, between the ligand analogue and the specific binding partner, may cause a change (e.g. a decrease) in the ability of electrons to flow e.g. from the enzyme to the electrode and vice versa via the mediator. This may, for example result from:

1. the blockage of access between the mediator and the enzyme by the formation of the complex, thus impairing electron transfer;
2. the blockage of access between the mediator and the electrode by the formation of the complex, thus impairing electron transfer;
3. alteration of the conformation of the mediator by the formation of the complex so that the free passage of electrons between the enzyme and mediator is inhibited; or 4. alteration of the conformation of the mediator by the formation of the complex so that the free passage of electrons between the mediator and electrode is inhibited.

In a typical homogeneous assay, therefore, formation of the complex perturbs an electrochemical characteristic of the components of the solution. It is not necessary for a full voltammogram to be determined in measuring the electrochemical characteristic; it may be sufficient, for example, for an appropriate poised potential to be selected and readings of current taken at that point. The degree of perturbation can then be related to the amount of ligand present in the sample, from calibration data obtained with similar system using known amounts of ligand.

Although the order of introduction of the components (a), (b) and, if present, (c) into the apparatus may not be critical, it is preferable that a complex is formed after introduction of the final one of components (a), (b) and, if present, (c), but not prior thereto. It is, however, also possible for there to be complex present before the final one of these components is added, in which case the final component will become complexed by displacing one component of the complex. It may be necessary to incubate these components for a period of time to allow the complexing reaction to approach equilibrium before component (d) is added. Addition of component (d) should not affect the complexing reaction, but these components must be present before measurements can be taken at the working electrode.

The method of the present invention is applicable to e.g. 'direct' assays (in which component (c) is absent), 'displacement' assays or 'competitive' assays (in which a ligand analogue is present in component (c)). The method of the invention may employ the so-called "sandwich" technique, using a solid phase binding partner. Depending on the order of the complexing reactions, the forward, fast forward, reverse and simultaneous variations are all possible according to the present invention. The solid phase may comprise the electrode surface, or may take the form of particles, beads etc. The solid phase binding partner may be prepared by any one of a number of conventional techniques for immobilising reagents onto solid supports.

In a method of the invention exploiting the time (t) parameter, the rate of perturbation of the electrochemical characteristic as a result of complex formation may be determined. Conveniently, the initial rate of perturbation will be measured. Such a method is applicable, for example, to a competitive assay in which the ligand and labelled ligand analogue compete for complexing with the specific binding partner. Thus, the initial rate of perturbation is related to the concentration of ligand present and from a calibration plot the initial rate of perturbation v. concentration of ligand present, the ligand assay can be readily determined.

The method of assay involving a determination of the rate of perturbation is also applicable to non-competitive assays where the labelled ligand analogue is absent and sufficient labelled specific binding partner is employed to enable all the ligand introduced to be complexed.

Measurement of, for example, the absolute electrochemical current generated after a standard incubation period may enhance the ease and sensitivity of the assay.

In a typical heterogeneous assay, formation of the complex causes no (or only a slight) perturbation in an electrochemical characteristic of the components. In that case, it is necessary artificially to generate or enhance a perturbation by means of a controlled external influence. Although the magnitude of the external influence may have some bearing on the change induced, and must therefore be consistent with any such influence employed in calibration experiments, it is thought that any change produced in the perturbation remains a function of the ligand/specific binding partner complex.

The artificial generation or enhancement of the perturbation is preferably performed by displacement of the complex relative to the unbound labelled component, for example by providing component (b) in an insolubilised form coupled (e.g. in conventional manner) to a solid support. Alternatively, the complex can be further complexed with a species which will bind specifically to the complex, coupled to a solid support, with subsequent displacement of the support and coupled molecules. In extreme cases, the displacement may constitute complete removal of the complex from the apparatus, but in general the complex will be displaced within the apparatus.

The solid support may, for example, comprise the electrode surface or may take the form of conventional solid phase particles, beads etc. The solid support may be magnetic or magnetisable to facilitate displacement or separation. Thus, for example, magnetic supports (e.g. in the form of particles or beads) may be composed of ferromagnetic or paramegnetic materials such as metals (e.g. iron, nickel or cobalt), metal alloys (e.g. magnetic alloys of aluminium, nickel, cobalt and copper), metal oxides (e.g. $Fe_3O_4$ $\gamma$-$Fe_3O_3$, $CrO_2$, $CoO$, $NiO$ or $Mn_2O_3$), magnetoplumbites or solid solutions (e.g. solid solutions of magnetite with ferric oxide). The preferred material for magnetic supports is magnetite ($Fe_3O_4$) or haematite ($\gamma$-$Fe_2O_3$). Particles may be non-colloidal or colloidal (e.g. of the type described in co-pending British Patent Application No. 8500092).

Displacement of the solid support, may, for example, be effected by urging the support into the vicinity of the electrode. In the case of magnetic supports (e.g. particles) the methods described in copending British Patent Application No. 8417538 may suitably be employed. Thus, for example, a magnetic electrode (e.g. comprising a permanent magnet or an electromagnet) may be used, or a non-magnetic electrode may be used in which case the particles will be urged into and retained in the vicinity of the electrode by the application of an external magnetic field.

The component (b) may be immobilised directly on to the magnetic support, or may be immobilised via one or more other 'spacer' molecules, including partners in specific binding interactions. Immobilisation of reagents may generally be achieved by conventional techniques such as, for example, adsorbtion, covalent bonding or cross-linking, or a combination of these techniques, e.g. adsorption of a chemical with one or more functional groups followed by covalent bonding or cross-linking of the reagent. Alternatively, substantially non-chemical means may be employed. Suitable immobilisation techniques are known in the art.

Other methods for artifically generating or enhancing the perturbation include, for example, removing excess uncomplexed labelled reagent, e.g. by draining from the apparatus or by coupling to a suitable solid support and removing the said solid support from the apparatus.

All of the variations described above for homogeneous assays (including direct, competitive, sandwich and displacement techniques and methods in which a rate of perturbation is measured rather than an absolute perturbation) are equally applicable to heterogeneous assays.

The methods of the present invention may generally be simpler than known methods, in that they may eliminate the need for separation of uncomplexed and complexed phases before the assaying step. However, as indicated above, the invention also includes within its scope methods in which reagents are employed immobilised on a solid surface, in which methods it may be necessary or desirable to separate the solid (complexed) and uncomplexed phases before the assaying step. Such separation may take the form of complete removal of the solid phase from the assay medium or may, for example, take the form of sedimentation or concentration of the solid phase in one region of the assay medium.

If electrode-immobilised components are employed, the need for separate addition of the component to the electrochemical apparatus may be eliminated. Additionally, the direct interaction between the electrode and the electrode-immobilised species may lead to an improvement in the sensitivity of the perturbation measurements.

According to a further feature of the present invention, therefore, there are provided methods of assay of a ligand in a sample as hereinbefore defined wherein one or more of the components (b) and, if present, (c) is/are immobilised on the working electrode or a suitable solid surface. The immobilized component(s) may be bound to the working surface of the working electrode or to a portion of the working electrode other than the working surface.

The immobilised component is preferably that component which is labelled. The said component may be immobilised via the label as long as the ability of the label to mediate electron transfer is not impaired.

Thus, for example, a polyviologen label may be covalently bonded to a metal electrode. The large polyviologen molecule projects from the electrode surface and this is believed to facilitate interaction with the enzyme. Alternatively, chloranil and/or fluoranil may be disseminated throughout an electrode composed of particulate carbon.

In one embodiment, the system comprises an electrode, e.g. a carbon (for example pyrolytic graphite) electrode, or a suitable solid surface carrying an immobilised layer of ferrocene dicarboxylic acid, 1,1'-dimethylferrocene (DMF) or polyvinylferrocene (having an average molecular weight of about 16000), the molecules of which are also coupled to reagent (b) or, if present (c), as labels thereof.

The carbon electrode core or suitable solid surface can be integral or a stiff paste of particles. Normally, any solid surface employed will present a porous surface for the ferrocene or ferrocene derivative, which may be adhered thereto in a number of ways, for examples:

(a) for monomeric ferrocene or a monomeric ferrocene derivative, by deposition from a solution in a readily evaporatable liquid e.g. an organic solvent such as toluene;

(b) for a ferrocene polymeric derivative, e.g. polyvinyl-ferrocene of average molecular weight about 16000 (for a method of synthesis see J. Polymer Sci. 1976, 14, 2433), deposition from a readily evaporatable organic solvent for the polymer such as chloroform;

(c) for a polymerisable ferrocene-type monomer, by electrochemically induced polymerisation in situ, e.g. by dissolving vinylferrocene in an organic electrolyte containing tertiary butyl ammonium perchlorate in concentration about 1M and depositing at a potential of −700 mV to induce deposition of vinylferrocene radicals as a polymer in situ; or (d) by covalent modification of the solid surface e.g. by carbdiimide cross-linking of the ferrocene or ferrocene derivative onto the surface (e.g. a carbon electrode).

Alternatively, the component may be immobilised directly on the solid surface by any of the conventional techniques used for coupling reagents to solid supports.

If desired, the electrode-immobilised component may be bound to a portion of the electrode other than the working surface. The electrode may in these circumstances be constructed so as to ensure that the immobilised component remains sufficiently close to the working surface to enable the assay to be carried out effectively. Such an electrode is illustrated in vertical cross-section in FIG. 2 of the accompanying drawings, this being particularly suitable for "sandwich" immunoassays in which the immobilised component is an unlabelled specific binding partner (e.g. a capture antibody). The electrode of FIG. 2 comprises an upwardly facing graphite working surface 1 in the base of a cell, the wall of which is formed by a polystyrene projection 2 from the body of the electrode. It is on this wall that a suitable specific binding partner may be immobilised (e.g. by adsorption). The electrical connection is provided by an insulated wire 3 secured to the bottom of the working surface by silver-loaded epoxy resin 4, the arrangement being encased in epoxy resin 5 and sealed with polypropylene 6.

It will be appreciated that, when component (b) is electrode-immobilised, it is not possible artifically to generate or enhance a perturbation by displacement of the resulting complex. However, a perturbation may still be artifically generated or enhanced, for example by complexing any uncomplexed labelled component remaining in solution with a species which will complex specifically with that component, coupled to a solid support, with subsequent displacement of the support and coupled molecules.

In a further aspect, the present invention provides kits of reagents and/or apparatus for carrying out the assays of the invention. Suitable kits may comprise an electrochemical apparatus containing a working electrode, an auxiliary electrode and optionally a reference electrode, and an aqueous assay medium with suitable components present (either in solution or immobilised). Other components (e.g. further reagents etc) and the sample to be assayed may conveniently be introduced through an entry port provided in the apparatus.

The apparatus may be automated so that the components are added in a predetermined sequence, and the incubation temperature may be controlled. Advantageously the apparatus may be pre-calibrated and provided with a scale whereby the perturbation in the electrochemical characteristic of the components may be read off directly as an amount of ligand in the sample.

Examples of ligands which may be assayed by the method of the invention are given in Table I below, together with an indication of a suitable specific binding partner in each instance.

TABLE I

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) |
| enzyme cofactor (substrate) | enzyme |
| lectins | specific carbohydrate |
| specific carbohydrate of lectins | lectins |

The method of the invention has very broad applicability, but in particular may be used to assay: hormones, including peptide hormones (e.g. thyroid stimulating hormone (TSH), human chorionic gonadotrophin (HCG), lutenising hormone (LH), follicle stimulating hormone (FSH), insulin and prolactin) or non-peptide hormones (e.g. steroid hormones such as cortisol, estradiol, progesterone and testosterone and thyroid hormones such as thyroxine (T4) and triiodothyronine), proteins (e.g. carcinoembryonic antigen (CEA) and alphafetoprotein (AFP)), drugs (e.g. digoxin), sugars, toxins or vitamins.

The invention will be particularly described hereinafter with reference to an antibody or an antigen as the ligand. However, the invention is not to be taken as being limited to assays of antibodies or antigens.

It will be understood that the term "antibody" used herein includes within its scope
(a) any of the various classes or sub-classes of immunoglobulin, e.g. IgG, IgM, derived from any of the animals conventionally used, e.g. sheep, rabbits, goats or mice,
(b) monoclonal antibodies,
(c) intact molecules or "fragments" of antibodies, monoclonal or polyclonal, the fragments being those which contain the binding region of the antibody, i.e. fragments devoid of the Fc portion (e.g., Fab, Fab', F(ab')2) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacteria fragments, cells, cell fragments and viruses) and haptens which may be rendered antigenic under suitable conditions.

Incorporation of, for example, a ferrocene label into the molecular structure of an antibody may for example be achieved by any of the following methods:
(i) providing the label with one or more functional groups capable of bonding interactions with the molecular structure of the antibody;
(ii) using cross-linking groups;
(iii) using the avidin-biotin binding system, (i.e. avidin-labelled antibody binding with biotin-labelled ferrocene molecules or biotin-labelled antibody binding with avidin-labelled ferrocene).

Similar methods may be applied as desired for labelling an antigen molecule. Suitable methods are known in the art and will not be discussed in detail here. For example, the incorporation of ferrocene into certain steroids is described in Journal of Organometallic Chemistry, 160 (1978) pp. 223-230.

Methods of purifying the labelled antibody or antigen are also known and include, for example, dialysis, density-gradient ultracentrifugation, gel filtration and ion-exchange chromatography.

The attachment of the label to the antibody or antigen can be via any portion of the molecular structure of the antibody or antigen, as long as immunological activity thereof is retained.

Immobilisation of an antibody or antigen molecule onto the electrode or other suitable solid surface may be effected by various methods. The attachment of the antibody or antigen to the electrode or solid surface can be via any portion of the molecular structure so long as specific immunological activity is retained at the antibody or antigen binding site.

Thus, for example, electrode-immobilisation of unlabelled antibody or antigen reagent may be achieved by bonding interactions between functional groups on the antibody or antigen molecule and the electrode, or by cross-linking or adsorption onto the surface of the electrode. Binding of reagents to the electrode may be accomplished by methods analogous to known methods for binding such reagents to solid supports (e.g. particles and beads), for example these described in European Patent Application No. 83305834.0

Electrode-immobilisation of labelled reagent, may, for example, be achieved by any of the following methods:
(i) incorporating a label molecule into the molecular structure of free reagent and subsequently immobilising the reagent onto an electrode at a site remote from the label in the same way as described above for unmodified reagents;
(ii) incorporating a label molecule into the molecular structure of a pre-immobilised reagent;
(iii) incorporating a bifunctional label into the molecular structure of free antibody or antigen so as to enable one function to interact with the electrode; or
(iv) incorporating a bifunctional label onto the electrode, so as to enable one function to interact with the molecular structure of free antibody or antigen.

The preferred label for use with an enzyme/substrate electron-source or electron-acceptor is ferrocene monocarboxylic acid.

When ascorbate is used as an electrode-source, and a catechol or aminophenol as a label, electrode-immobilisation of labelled reagent is preferably achieved by adsorption or chemical reaction via the label on a suitably modified carbon electrode. A discussion of methods of attachment of such species to carbon electrodes is given in Analytical Chemistry, Vol. 55, 9 (1983), p. 1576.

By way of example only, the invention includes inter alia the following embodiments:
$\succ$ = antibody, $\Diamond$ = antigen, M = mediator label, E = electron-source or acceptor (e.g. enzyme + substrate), $\exists$ = electrode surface, O = solid phase (non-electrode); ?indicates ligand under assay

1. Direct Antibody Assay

Soluble

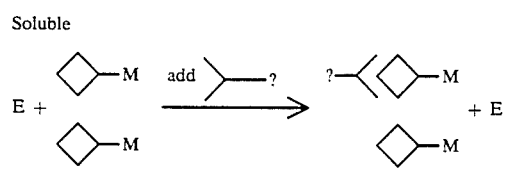

(a)

Immobilised on electrode

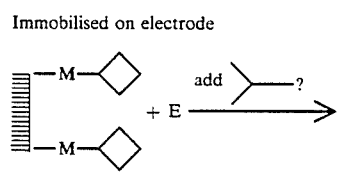

(b)

In both these assays the formation of the immune complex decreases the efficacy of the mediator, the change in signal being a measure of antibody concentration.

2. Direct Antigen Assay

Soluble

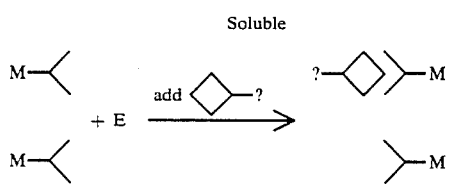

(a)

The immune reaction alters the ability of the mediator/antibody complex to shuttle electrons to or from the electrode. Therefore the signal changes.

Immobilised

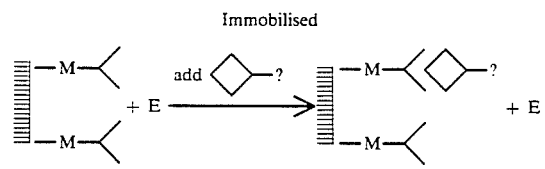

3. Competitive Antigen Assay

Soluble

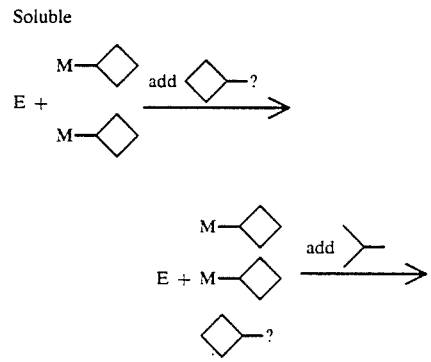

(a)

-continued

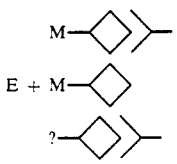

Competition between the mediator-labelled antigen and the antigen under assay for the available antibody results in some of the mediator being perturbed, the signal relating to the concentration of antigen under assay.

(b) Immobilised

The immobilised system can take two forms:

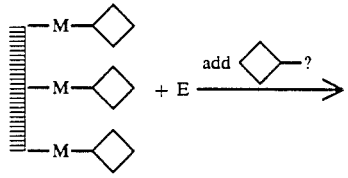

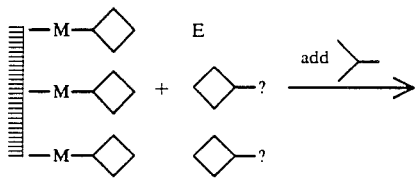

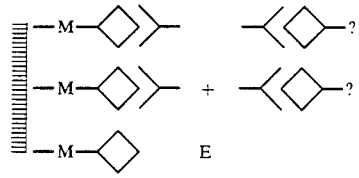

After separation, the signal measured depends upon the ratio of the antigen under assay to mediator-labelled antigen. The electrode supplies a means of easy separation.

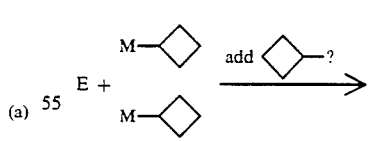

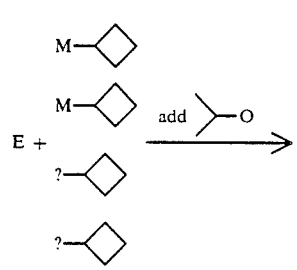

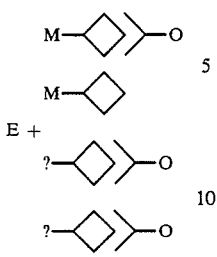

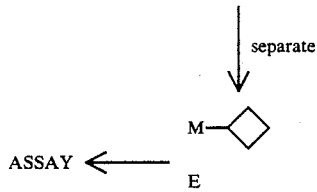

The sedimenting of the immune complex reduces the amount of mediator in solution hence perturbing the signal.

4. Displacement Antigen Assay

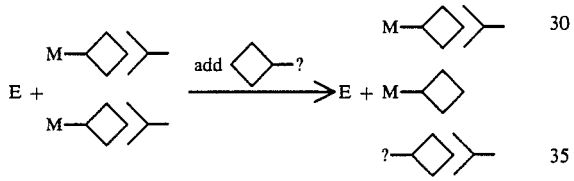

Displacement of mediator/antigen complex from the antibody of the antigen under assay results in an increase in signal.

5. Sandwich Antigen Assay

On electrode

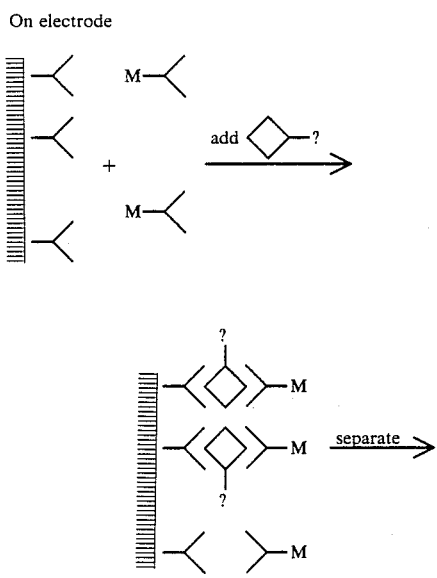

(a)

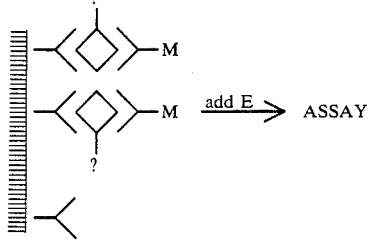

The binding of mediator-labelled antibody to the electrode via the antigen gives a measure of antigen concentration.

On solid phase (b)

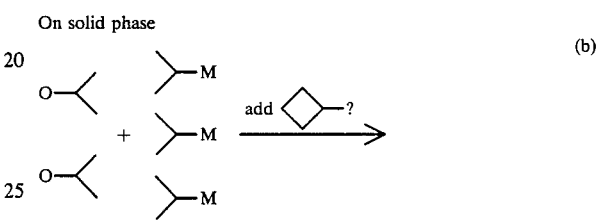

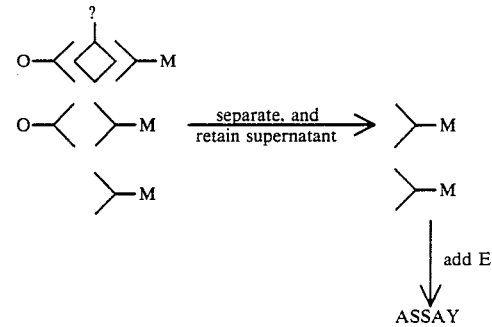

This will only work if the free mediator is assayed, but still gives a measure of antigen concentration.

6. Competitive Sandwich Antibody Assay

On electrode (a)

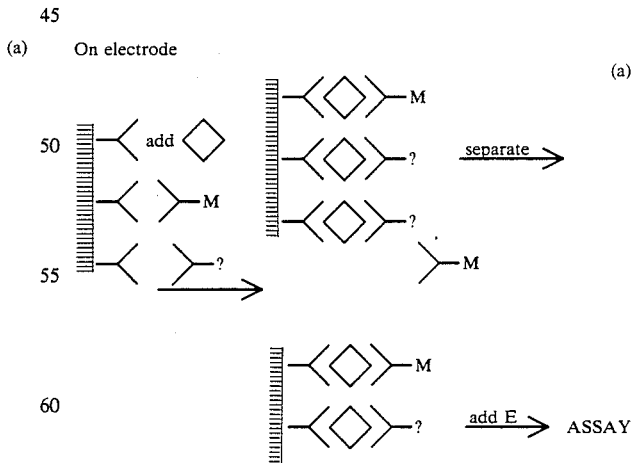

Competition between mediator-labelled antibody and the antibody under assay produces a signal which relates to the concentration of the antibody under assay.

On solid phase

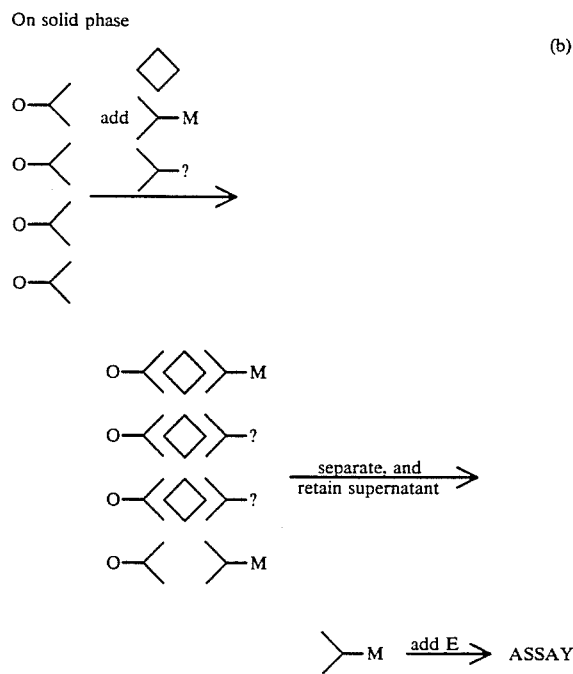

The mechanism of action is the same as the electrode immobilised system but the free mediator is used to give a signal.

The following Examples are intended to illustrate the invention more fully:

Example 1:

Evaluation of a conjugate of thyroxine (T4) and ferrocene monocarboxylic acid (FMCA) (T4-FMCA) as a mediator for glucose oxidase.

Preparation of starting materials (i) Ferrocene-modified thyroxine (T4) hormone (hapten)

To stirred cooled (−10° C.) dimethylformamide (3 mls), was added ferrocene monocarboxylic acid (FMCA) (1 mmol) and then triethylamine (1.0 mmole). The mixture was then further cooled to −15° C. and stirred for 30 minutes and then allowed to warm up to room temperature and stirred for a further hour. The resulting carboxycarbonic anhydride of ferrocene was added dropwise to a solution of T4 in sodium hydroxide/ethanol and stirred for 24 hours, after which the sample was filtered and then concentrated by rotary evaporation. The resulting precipitate was washed in carbon tetrachloride, then ethyl acetate several times, the insoluble ferrocene monocarboxylic acid-T4 conjugate (T4-FMCA) then being filtered out of the ethyl acetate solution.

(ii) Purification of Ferrocene-modified thyroxine conjugate (T4-FMCA)

The T4-FMCA conjugate was purified by high performance liquid chromatography using a C18 reverse phase column. After purification, the T4 and ferrocene concentrations in the conjugate were measured by radioimmunoassay and electrochemistry respectively.

(iii) Characteristics of the T4-FMCA conjugate

Incubation of T4-FMCA with excess anti-T4 antibody showed that 73.4% of the T4-FMCA was bound to the antibody.

Figure 4A:
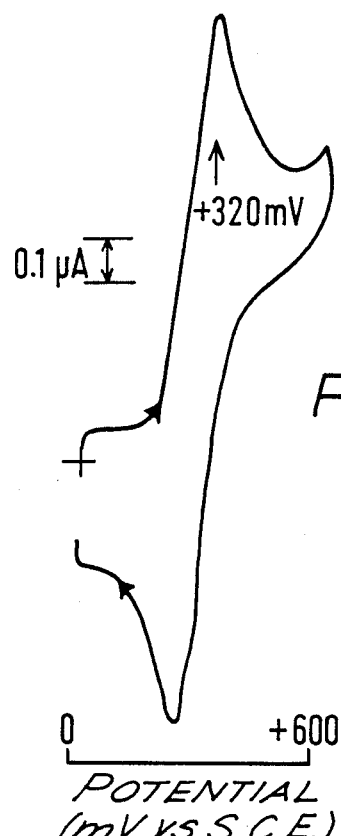
Figure 4B:
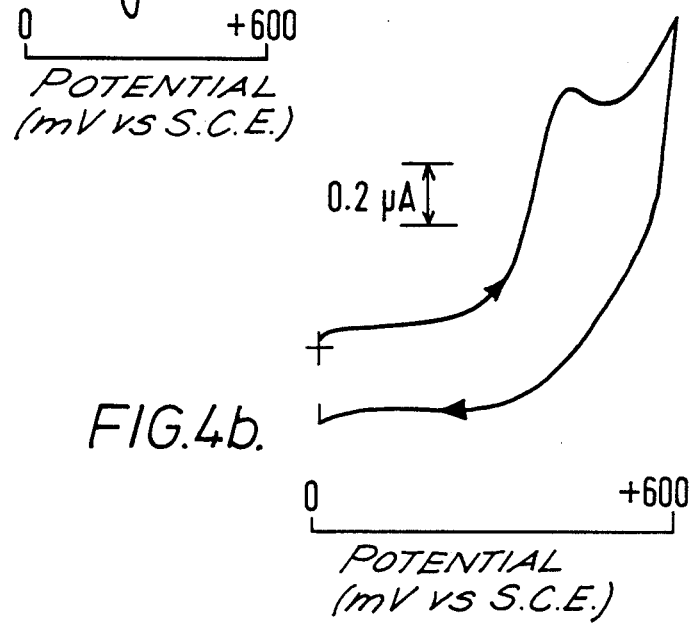

The electrochemistry of the conjugate was also compared with that of the T4 and FMCA. The conjugate shows two peaks on the forward wave of the cyclic voltammogram at a pyrolytic graphite electrode (Voltage Scan Rate=20 mVs−1), the first being at +310 mV vs a standard calomel electrode (S.C.E.) (the ferrocene peak), the second at +410 mV vs S.C.E. (T4) FIG. 3. On the return wave only one peak at a potential of +255 mV vs S.C.E. was observed. Cyclic voltammetry at pyrolytic graphite electrodes (Voltage Scan Rate=5 mVs−1) of the unmodified components of the conjugate showed that FMCA [0.2 mM FMCA in Tris (50 mM; pH 7.4] has peaks at +320 mV and +260 mV vs S.C.E. for the forward and return waves respectively (FIG. 4a) whilst T4 exhibits a single peak at +420 mV vs S.C.E. on the forward wave (FIG. 4b).

Anti-T4 Antibody

Anti-T4 antibody was a conventional polyclonal antiserum obtained by immunising sheep with T4 conjugated to a high molecular weight protein (keyhole limpet haemocyanin).

Standard Solutions of T4

T4 (sodium salt) was obtained from Sigma London Chemical Company, England. Standard solutions were made by disolving the T4 in sodium hydroxide (0.1M) and then diluting with Tris-HCl buffer (50 mM pH 7.4) to the desired concentration.

(vi) Apparatus used to measure the electrochemistry of T4-FMCA

Figure 1B:
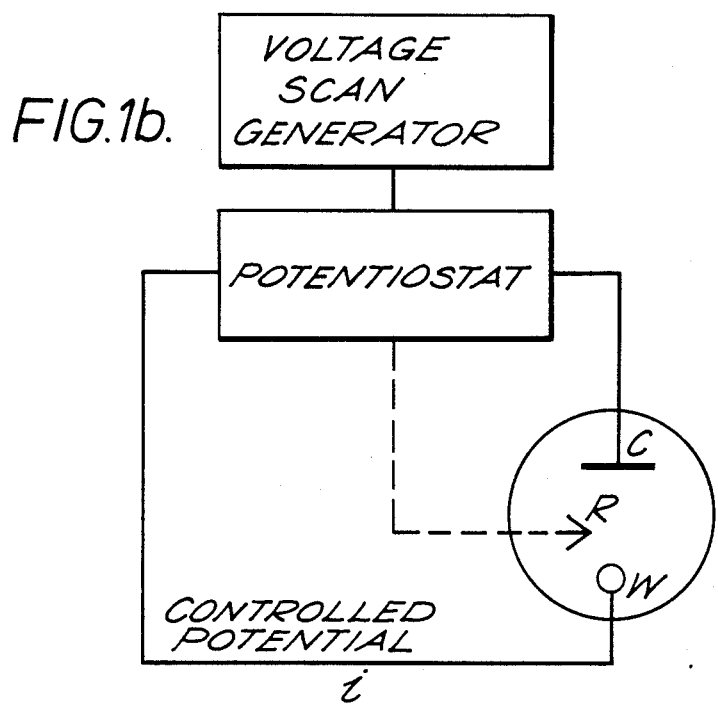

Cyclic voltammetry was performed using a three electrode electrochemical cell with a pyrolytic graphite working electrode as shown in FIG. 1(a).

Evaluation of the performance of the T4-FMCA conjugate as an electron transfer mediator for glucose oxidase 40 µl of a solution of T4-FMCA ($3 \times 10^{-7}$ molar, in sodium proprionate buffer, 200 mM/l, pH 6.0) was added to the electrochemical cell along with 40 µl of glucose (a molar solution containing 100 mM/l of magnesium chloride) and 320 µl of Tris/HCl buffer (10 mM/l, pH 7.4). After measurement of the electrochemical current, the above experiment was repeated with 20 µl of a solution of glucose oxidase (1 mg of enzyme per ml in water) added, but only 300 µl of buffer. Again the electrochemical current was measured.

In a third series of experiments, 20 µl of the anti-T4 antiserum was added to 40 µl of the T4-FMCA conjugate and 280 µl of the buffer. After an incubation period of 20 minutes, 20 µl of glucose oxidase solution and 40 µl of glucose solution were added and the electrochemical current remeasured.

In a fourth series of experiments, 20 µl of a solution of T4 (0.5 mM per liter in Tris/HLC buffer, 10 mM/l, pH 7.4), 20 µl of the anti-T4 antiserum, 40 µl of the T4-FMCA conjugate and 260 µl of Tris/HCl buffer were mixed and incubated for 20 minutes. After addition of 20 µl of the solution of glucose oxidase and 40 µl of the glucose solution, the electrochemical current was measured.

In all cases, the electrochemical current was measured at a temperature of 37±0.5° C. and at a voltage scan rate of 5 mV/S. The results are presented in Table 1.

The results show that the T4-FMCA will act as an electron transfer mediator for glucose oxidase, its ability to mediate being perturbed upon binding with anti-T4 antibody.

TABLE 1

| EXPERIMENT | ELECTROCHEMICAL CURRENT (μA) |
|---|---|
| T4-FMCA + glucose + buffer | 0.58 |
| T4-FMCA + glucose + buffer + glucose oxidase | 1.58 ± 0.04 |
| T4-FMCA + glucose + buffer + glucose oxidase + anti-T4-antibody | 1.35 ± 0.01 |
| T4-FMCA + glucose + buffer + glucose oxidase + anti-T4-antibody + T4 standard | 1.53 ± 0.05 |

Example 2: Ferrocene-modified IgG antibody

To a stirred cooled (−8° C.) solution of ferrocene monocarboxylic acid (1 mmole) in tetrahydrofuran (dried), isobutyl chloroformate (1 mmole) and triethylamine (1 mmole) were added with stirring. The mixture was stirred for thirty minutes and then allowed to warm up to room temperature and stirred for a further hour. The resulting carboxycarbonic anhydride of ferrocene was added dropwise to a cooled (2° C.) solution of IgG (500 mg) in 50 ml of 0.1M sodium bicarbonate solution. The reaction mixture was stirred at 4° C. for 24 hours and then dialysed exhaustively against borate buffer pH 8.5. It was spun and gel filtered on S-200 gel. The iron content was determined by atomic absorption.

We claim:

1. In a homogeneous method of assaying a ligand in a sample using electrochemical apparatus containing a working electrode and components comprising:
   (a) the sample, and
   (b) a specific binding partner to the ligand, or a specific binding partner to the ligand and at least one further reagent selected from ligand analogues and specific binding partners to the ligand, the improvement which comprises said components including
   (c) an electron-source or electron-acceptor selected from oxidoreductase enzymes in cooperation with a substrate therefor and non-enzyme electron sources;
   one of components (b) being labelled with an electron-transfer mediator capable of aiding the transfer of electrons between the electron-source or electron-acceptor and the working electrode by accepting electrons from the electron-source and donating them to the working electrode, or accepting electrons from said electrode and donating them to the electron-acceptor; and
   which method includes the step of determining whether the said transfer of electrons is perturbed by formation of a complex of said ligand with a specific binding partner.

2. A method as claimed in claim 1 wherein component (c) is an oxidoreductase enzyme in co-operation with a substrate therefor.

3. A method as claimed in claim 1 wherein the electron-transfer media comprises ferrocene or a derivative thereof.

4. A method as claimed in claim 3 wherein the electron-transfer mediator comprises a derivative of ferrocene containing one or more side chains of the formula —CHO, —$(CH_2)_n$ COOH or —$(CH_2)_m$ $NR^1R^2$ (where n and m are each from 0 to 6) and $R^1$ and $R^2$, which may be the same or different, each represents hydrogen or an alkyl group containing 1 to 4 carbon atoms).

5. A method as claimed in claim 1 wherein the perturbation in the transfer of electrons is determined from a perturbation in the peak current observed under the application of a preselected potential across the components.

6. A method as claimed in claim 1 wherein the ligand is an antigen or an antibody.

7. A method as claimed in claim 1, wherein the extent to which the said transfer of electrons is perturbed is determined, the extent of perturbation being an indication of the amount of ligand in the sample.

8. A method as claimed in claim 2, wherein the extent to which the said transfer of electrons is perturbed is determined, the extent of perturbation being an indication of the amount of ligand in the sample.

9. A method as claimed in claim 7, wherein said electron source is ascorbate or NADH.

10. A method as claimed in claim 1, wherein said electron source is ascorbate or NADH.

11. A kit for carrying out a method of assay as claimed in claim 1 comprising in at least one container: (i) at least one specific binding partner to the ligand or a specific binding partner to the ligand and at least one further reagent selected from ligand analogues and specific binding partners to the ligand one of the components (i) being labelled with an electron transfer mediator, and (ii) a non-enzyme electron-source capable of donating electrons to said electron transfer mediator.

12. A kit as claimed in claim 11 which further comprises an electrochemical apparatus containing a working electrode.

13. A kit for carrying out a method of assay as claimed in claim 2 comprising in separate containers: (i) at least one specific binding partner to the ligand or a specific binding partner to the ligand and at least one further reagent selected from ligand analogues and specific binding partners to the ligand, one of the components (i) being labelled with an electron transfer mediator; and (ii) an oxidoreductase enzyme which in cooperation with a substrate therefor is capable of donating electrons to said electron transfer mediator or accepting electrons from said electron transfer mediator.

14. A kit as claimed in claim 13 which further comprises an electrochemical apparatus containing a working electrode.

15. A method as claimed in claim 1 wherein a specific binding partner to the ligand or a ligand analogue is immobilized on the working electrode.

16. In a heterogeneous method of assaying a ligand in a sample using electrochemical apparatus containing a working electrode and components comprising:
   (a) the sample, and
   (b) the specific binding partner to the ligand, or a specific binding partner to the ligand and at least one further reagent selected from ligand analogues and specific binding partners to the ligand, the improvement which comprises said components including (c) an electron-source or electron-acceptor selected from oxidoreductase enzymes in cooperation with a substrate therefor and non-enzyme electron sources;

one of components (b) being labelled with an electron-transfer mediator capable of aiding the transfer of electrons between the electron-source or electron-acceptor 17. A method as claimed in claim 16 wherein component (c) is an oxidoreductase enzyme in cooperation with a substrate therefor.

18. A method as claimed in claim 16 wherein the electron-transfer mediator comprises ferrocene or a derivative thereof.

19. A method as claimed in claim 16 wherein the ligand is an antigen or an antibody.

20. A method as claimed in claim 16, wherein the extent to which the said transfer of electrons is perturbed is determined, the extent of perturbation being an indication of the amount of ligand in the sample.

21. A method as claimed in claim 16 wherein an unlabelled specific binding partner to the ligand under assay is immobilized on a solid support.

22. A kit for carrying out a method of assay as claimed in claim 16 comprising in at least one container:
  (i) at least one specific binding partner to the ligand or a specific partner to the ligand and at least one further reagent selected from ligand analogs and specific binding partners to the ligand, one of the components (i) being labelled with an electron-transfer mediator, and (ii) a non-enzyme electron-source capable of donating electrons to said electron transfer mediator.

23. A kit for carrying out a method of assay as claimed in claim 16 comprising in separate containers:
  (i) at least one specific binding partner to the ligand or a specific binding partner to the ligand and at least one further reagent selected from ligand analogs and specific binding partners to the ligand, one of the components (i) being labelled with an electron-transfer mediator; and (ii) an oxidoreductase enzyme which in cooperation with a substrate therefor is capable of donating electrons to said electron transfer mediator or accepting electrons from said electron transfer mediator. and the working electrode by accepting electrons from the electron-source and donating them to the working electrode, or accepting electrons from said electrode and donating them to the electron-acceptor; and which method includes the steps of (i) providing means for displacement of any mediator-labelled complex containing said ligand relative to any other mediator-labelled component, or where a mediator-labelled ligand analogue is present as component (b), providing means for displacement of any complex containing said ligand analog relative to non-complexed mediator-labelled ligand analog and (ii) determining whether the said transfer of electrons is thereby perturbed.

* * * * *

UNITED STATES PATENT AND TRADEMARK OFFICE
CERTIFICATE OF CORRECTION

PATENT NO. : 4,945,045

DATED : July 31, 1990

INVENTOR(S) : Forrest et al

It is certified that error appears in the above-identified patent and that said Letters Patent is hereby corrected as shown below:

On the title page, item [73] should be deleted in its entirety.

Signed and Sealed this

Thirty-first Day of December, 1996

Attest:

BRUCE LEHMAN

*Attesting Officer*      *Commissioner of Patents and Trademarks*